(12) United States Patent
Venkatraman et al.

(10) Patent No.: US 10,548,769 B2
(45) Date of Patent: Feb. 4, 2020

(54) GLAUCOMA VALVE, A CASING FOR CONTAINING A GLAUCOMA VALVE, AND A GLAUCOMA DRAINAGE DEVICE COMPRISING THE VALVE AND/OR THE CASING

(75) Inventors: Subramanian Venkatraman, Singapore (SG); Lei Shang, Singapore (SG); Yin Chiang Freddy Boey, Singapore (SG); Tina Wong, Singapore (SG)

(73) Assignees: NANYANG TECHNOLOGICAL UNIVERSITY, Singapore (SG); SINGAPORE HEALTH SERVICES PTE LTD., Singapore (SG)

( * ) Notice: Subject to any disclaimer, the term of this patent is extended or adjusted under 35 U.S.C. 154(b) by 336 days.

(21) Appl. No.: 13/816,631

(22) PCT Filed: Aug. 12, 2011

(86) PCT No.: PCT/SG2011/000283
§ 371 (c)(1),
(2), (4) Date: Apr. 22, 2013

(87) PCT Pub. No.: WO2012/021109
PCT Pub. Date: Feb. 16, 2012

(65) Prior Publication Data
US 2013/0211314 A1    Aug. 15, 2013

Related U.S. Application Data

(60) Provisional application No. 61/372,951, filed on Aug. 12, 2010.

(51) Int. Cl.
*A61F 9/007* (2006.01)
(52) U.S. Cl.
CPC ............................... *A61F 9/00781* (2013.01)

(58) Field of Classification Search
CPC ... A61F 9/00781; A61F 9/007; A61M 27/002; A61M 2210/0612
See application file for complete search history.

(56) References Cited

U.S. PATENT DOCUMENTS

| 4,722,724 A | 2/1988 | Schocket |
| 5,071,408 A | 12/1991 | Ahmed |

(Continued)

FOREIGN PATENT DOCUMENTS

| CN | 101360523 A | 2/2009 |
| WO | WO 2007/087061 A2 | 8/2007 |
| WO | WO 2010/068467 A1 | 6/2010 |

OTHER PUBLICATIONS

Shishatskaya, E. I., et al. "Tissue response to the implantation of biodegradable polyhydroxyalkanoate sutures." Journal of Materials Science: Materials in Medicine 15.6 (2004): 719-728.*

(Continued)

*Primary Examiner* — Adam Marcetich
(74) *Attorney, Agent, or Firm* — Alston & Bird LLP (57) ABSTRACT

Provided is a glaucoma valve, a casing for containing a glaucoma valve and a glaucoma drainage device including the glaucoma valve and/or the casing. The valve includes a flow channel having an inlet and an outlet and a valve member connected to the outlet of the flow channel. The valve member may be formed from a degradable polymer or a combination of degradable polymer and non-degradable polymer. The valve may have a first flow channel, the interior of which may be coated with a degradable polymer, such that in use, the polymer degrades to allow a greater flow of fluid through the flow channel. The valve may include a second flow channel, which may be arranged in parallel to the first flow channel. The casing may be formed from a degradable polymer, such as a biodegradable polymer.

19 Claims, 7 Drawing Sheets

(56) References Cited

U.S. PATENT DOCUMENTS

| | | | |
|---|---|---|---|
| 6,558,342 | B1 | 5/2003 | Yaron et al. |
| 2003/0158598 | A1 | 8/2003 | Ashton et al. |
| 2004/0162545 | A1 | 8/2004 | Brown et al. |
| 2005/0288617 | A1 | 12/2005 | Yaron et al. |
| 2006/0160984 | A1* | 7/2006 | Nagasawa et al. ............ 528/272 |
| 2008/0086199 | A1* | 4/2008 | Dave et al. .................. 623/1.42 |
| 2008/0152694 | A1* | 6/2008 | Lobl et al. .................... 424/427 |
| 2008/0227905 | A1* | 9/2008 | Kumasaki et al. ............ 524/505 |
| 2009/0004243 | A1* | 1/2009 | Pacetti et al. ................. 424/426 |
| 2009/0182415 | A1* | 7/2009 | Wang .......................... 623/1.49 |
| 2009/0264391 | A1* | 10/2009 | King ............................ 514/174 |
| 2009/0280158 | A1* | 11/2009 | Butuner ........................ 424/428 |
| 2010/0004734 | A1* | 1/2010 | Ramzipoor et al. ......... 623/1.15 |
| 2010/0331980 | A1* | 12/2010 | Lee et al. ................... 623/14.13 |
| 2011/0230963 | A1* | 9/2011 | Cuevas ........................ 623/6.56 |
| 2011/0306915 | A1 | 12/2011 | De Juan, Jr. et al. |
| 2012/0165957 | A1* | 6/2012 | Everland et al. .......... 623/23.72 |

OTHER PUBLICATIONS

Office Action from corresponding Chinese Patent Application No. 201180039894.X, dated Jul. 18, 2014.

International Search Report for Application No. PCT/SG2011/000283, dated Sep. 3, 2012.

International Search Report and Written Opinion for Application No. PCT/SG2011/000283, dated Oct. 18, 2011.

Jones, R. IIII, *Corticosteroid-induced Ocular Hypertension and Glaucoma: A Brief Review and Update of the Literature*, Current Opinion in Ophthalmology, vol. 17 (2006)pp. 163-167.

Middleton, J.C., et al., *Synthetic Biodegradable Polymers as Medical Devices* [online][retrieved May 17, 2013 ]Retrieved from: <URL: http://www.mddionline.com/article/synthetic-biodegradable-polymers-medical-devices >dated Mar. 1, 1998.

Quigley, H.A., et al, *The Number of People with Glaucoma Worldwide in 2010 and 2020*, Br J Ophtalmol 90 (2006) pp. 262-267

Kafkala, C. et al., *Ahmed Valve Implantation for Uncontrolled Pediatric Uveitic Glaucoma*, Journal of AAPOS, Vol. 9, No. 4 (Aug. 2005) 336-340.

Lim, K. S., *Experimental Flow Studies in Glaucoma Drainage Device, Development*, Br. J. Ophthalmol 85 (2001) 1231-1236.

Nouri-Mandavi, K. et al., *Evaluation of the Hypertensive Phase After Insertion of the Ahmed Glaucoma Valve*, American Journal of Ophthalmology, vol. 136, No. 6 (Dec. 2003) 1001-1008.

Quigley, H.A. et al., *The Number of People with Glaucoma Worldwide in 2010 and 2010*, BR J Ophthalmol 90 (2006) 262-267.

Stay, M. S. et al., *Thin-Film Coupled Fluid-Solid Analysis of Flow Through The Ahmed™ Glaucoma Drainage Device*, Transactions of the ASME, vol. 127 (Oct. 2005) 776-781.

Schwartz, K. S. et al., *Glaucoma Drainage Implants: A Critical Comparison of Types*, Curr Opin Ophthalmol 17 (2006) 181-189.

*The Advanced Glaucoma Intervention Study (AGIS): 7. The Relationship Between Control of Intraocular Pressure and Visual Field Deterioration*, American Journal of Ophthalmology, vol. 130, No. 4 (Oct. 2000) 429-440.

Ionomers: Synthesis, structure, properties and application, edited by M.R. Tant, K.A. Mauritz, G.L. Wilkes, pp. 444-445 (1997).

Supplementary European Search Report for Application No. EP 11 81 6699 dated Feb. 25, 2015.

\* cited by examiner

(Prior art)

GLAUCOMA VALVE, A CASING FOR CONTAINING A GLAUCOMA VALVE, AND A GLAUCOMA DRAINAGE DEVICE COMPRISING THE VALVE AND/OR THE CASING

CROSS-REFERENCE TO RELATED APPLICATIONS

This application makes reference to and claims the benefit of priority of an application for "Two-Channel Glaucoma Valve For An Improved Glaucoma Drainage Device" filed on Aug. 12, 2010 with the United States Patent and Trademark Office, and there duly assigned Ser. No. 61/372,951. The content of said application filed on Aug. 12, 2010 is incorporated herein by reference in its entirety for all purposes.

TECHNICAL FIELD

The invention relates to a glaucoma valve, a casing for containing a glaucoma valve and a glaucoma drainage device comprising the valve and/or the casing.

BACKGROUND

Glaucoma is an ocular disorder associated with elevated intraocular pressures (IOP) that are too high for normal ocular activity and may result in an irreversible loss of visual function. In a human eye for example, a fluid called the aqueous humor functions to maintain pressure in the eye at a range of about 10 to 21 mm Hg. The aqueous humor is constantly secreted by the ciliary body, and functions to keep the globe of the eye firm while providing nutrition for the lens and the cornea. The aqueous humor is drained away at the base of the iris via a series of channels known as the trabecular meshwork back into the bloodstream. When the aqueous humor drains properly, an appropriate fluid pressure is maintained in the eye. However, when these outflow channels become blocked, the pressure in the eye may increase due to built-up of the aqueous humor in the eye, and the circulation of blood to the optic nerve and other parts of the eye may be restricted. If the intraocular pressure remains elevated for prolonged time periods, the fibers of the optic nerve may atrophy and the retina may lose function, leading to glaucoma. If left untreated, glaucoma may eventually lead to blindness. Approximately 70 million people are affected world-wide, of whom 6.7 million suffer from bilateral blindness (Quigley H. A. et al., *Br J Ophthalmol*, 2006, 90, 262-7).

Presently, glaucoma is not curable by any available treatment method. However, various options are available to control and perhaps delay the progression of the disorder. State of the art methods to treat glaucoma include medicinal therapy and surgery. In medicinal therapy, eye drops containing a pharmaceutical agent, such as latanoprost and levobunolol, are usually prescribed to the patient for self-administration to the affected eye(s). The eye drops may work by improving outflow of aqueous humor from the eye and/or decrease production of aqueous humor by the ciliary body. However, this method may suffer from disadvantages such as undesirable side effects as a result of the medications and ineffective treatment due to poor compliance with medication administration procedures.

In some cases, medicinal therapy alone may not be sufficient to alleviate pressure built-up in the eye. Under these circumstances, surgery may be performed as a next step in glaucoma treatment. Examples of surgical methods for the treatment of glaucoma include trabeculectomy, laser surgery and implantation of glaucoma drainage devices.

In a trabeculectomy, a partial thickness scleral flap is made in the scleral wall of the eye and an opening is made under the flap to excise a section of trabecular meshwork. The scleral flap is then loosely sewn back into place so as to allow continuous drainage of the aqueous humor fluid. Post-operatively, the aqueous humor may flow out of the eye through the opening and may be absorbed through the bloodstream, thereby resulting in a lowered IOP. However, this method may cause excessive scarring around or over the flap, which could decrease the amount of, or prevent the flow of, aqueous humor fluid from the eye. Consequently, IOP may not be adequately lowered. In other cases, there may be excessive filtering of the aqueous humor fluid from the eye, a condition termed as hypotemy, which may result in an IOP value that is too low.

In laser surgery, thermal energy from a laser is applied to a number of spots in the trabecular meshwork, with the object to facilitate outflow of aqueous humor from the eye in order to lower the IOP. However, this method suffers from complications such as inflammation of the trabecular meshwork and tissue scarring.

In some cases, the doctor may recommend implanting a glaucoma drainage device (GDD) in the affected eye(s). Generally, a GDD is implanted when glaucoma cannot be controlled using medication, trabeculectomy or laser surgery. It may also be used in cases where trabeculectomy or laser surgery would likely fail. The GDD works to provide an avenue in which aqueous humor fluid can be drained from the eye so as to lower the IOP. State of the art GDD includes a tube that is attached to a plate, such as that for an Ahmed GDD or a Baerveldt® GDD. Generally, implanting the GDD includes excising the conjunctiva to expose the eye muscles, placing the plate of the GDD between or underneath the eye muscles, and fastening the plate to the underlying sclera with permanent sutures. The tube of the GDD is then cut to appropriate length and inserted into the anterior chamber of the eye. The conjunctiva is subsequently put into place over the plate to cover the tube.

Even though the success rate of GDD implantation is generally high, however, there still exist issues that may be encountered after implantation of the GDDs. These include a) an abnormally low initial IOP, which may occur within weeks from implantation, and b) an abnormally high late IOP, which may occur several months after implantation. Of these, an abnormally high IOP that occurs later on post operation is generally deemed to be more serious as it is believed to be responsible for device failure in the majority of patients.

An abnormally high late IOP may occur due to formation of a fibrous capsule around the GDD as part of a natural wound healing process after invasive surgery. The fibrous capsule may increase the flow resistance by at least partially obstructing the drainage of aqueous humor fluid from the eye, thereby resulting in a higher IOP value compared to the period of time before capsule formation. Current state of the art GDDs are not able to mitigate the increase in IOP resulting from fibrous capsule formation. As a result, further surgical intervention is required for glaucoma control.

In view of the above, there remains a need for an improved glaucoma drainage device.

SUMMARY OF THE INVENTION

In a first aspect, the invention relates to a glaucoma valve. The valve comprises a) a flow channel having an inlet and an outlet; and
b) a valve member connected to the outlet of the flow channel, wherein the valve member comprises a degradable polymer.

In various embodiments of the valve, the degradable polymer is a biodegradable elastomer. The biodegradable elastomer may be polylactic acid (PLA), polycaprolactone (PCL), poly(glycolide) (PLGA), a copolymer of PLA and PCL, a copolymer of PLA, PCL and PLGA, a copolymer of PLA, PCL and trimethylene carbonate (TMC), or a copolymer of PLA, PCL, TMC and polyurethane (PU). In one embodiment of the inventive valve, the copolymer of PLA and PCL has a molar ratio of about 7:3. In various embodiments, the copolymer of PLA and PCL is a multiblock copolymer of PLA and PCL, or a triblock copolymer of PLA and PCL having PLA as the end-blocks and PCL as the middle block. The multiblock copolymer of PLA and PCL may be PCL-PLA-co-PLA-PCL, having a caprolactone content of about 30% in the first block and an lactic acid content of about 30% in the second block. The PLA end-blocks of the triblock copolymer of PLA and PCL may have a crystallinity of about 10% to about 20%. In various embodiments, the copolymer of PLA, PCL and PLGA is a triblock copolymer having PLA as the end-blocks and a random copolymer of PCL and PLGA as the middle block. In various embodiments, the copolymer of PLA, PCL and TMC is a triblock copolymer having PLA as the end-blocks and a random copolymer of PCL and TMC as the middle block. In one embodiment, the PLA end-blocks of the triblock copolymer of PLA, PCL and TMC has a crystallinity of about 10% to about 20%. In various embodiments, the copolymer of PLA, PCL, TMC and PU is a polyurethane with PCL/PLA and PCL/TMC soft segments.

In various embodiments of the inventive valve, the polymer has a Young's modulus of about 1 MPa to about 30 MPa. In some embodiments, the polymer has an elongation to break percentage of greater than about 100%. In some embodiments, the polymer has an elastic recovery value of greater than about 80%.

In various embodiments, the valve member has a length of about 1 mm to about 10 mm.

In various embodiments, the valve member further comprises a steroid. The steroid may be, for example, dexamethasone, fluocinolone, fluocinolone acetonide, triamcinolone, triamcinolone acetonide, salts thereof, derivatives thereof, or mixtures thereof. The steroid may be coated on the surface of the valve member.

In a second aspect, the invention relates to a glaucoma valve. The valve comprises a first flow channel. The interior of the first flow channel is at least in part coated with a degradable polymer, such that in use, the polymer degrades to allow a greater flow of fluid through the flow channel.

In various embodiments, the polymer is a biodegradable polymer. The biodegradable polymer may be polylactic acid (PLA), polycaprolactone (PCL), poly(glycolide) (PLGA), a copolymer of PLA and PCL, a copolymer of PLA, PCL and PLGA, a copolymer of PLA, PCL and trimethylene carbonate (TMC), or a copolymer of PLA, PCL, TMC and polyurethane (PU).

In various embodiments, the glaucoma valve further comprises a second flow channel. The second flow channel may be arranged in parallel to the first flow channel. In some embodiments, the second flow channel is connected in parallel to the first flow channel. For embodiments having a second flow channel, the first flow channel may be completely sealed with the polymer, such that in use, the polymer degrades to allow fluid to flow through the first flow channel.

In a third aspect, the invention relates to a casing for containing a glaucoma valve. The casing may have a top portion and a bottom portion. Either or both the top portion and the bottom portion may be formed from a biodegradable polymer. In some embodiments, the biodegradable polymer is PLGA. The PLGA may have a lactic acid to glycolic acid ratio of about 3:1 to about 9:1. The biodegradable polymer may have a Young's modulus of about 10 to about 1000 MPa. The biodegradable polymer may have a degradation time of about 3 weeks to about 12 weeks.

In a fourth aspect, the invention relates to a glaucoma drainage device comprising a glaucoma valve according to the first aspect or the second aspect, or a casing according to the third aspect.

In a fifth aspect, the invention relates to use of a glaucoma drainage device according to the fourth aspect for the drainage of aqueous humor in an eye.

BRIEF DESCRIPTION OF THE DRAWINGS

The invention will be better understood with reference to the detailed description when considered in conjunction with the non-limiting examples and the accompanying drawings, in which:

FIG. 1A to FIG. 1D are schematic diagrams of a glaucoma valve 100 according to an embodiment of the first aspect of the present invention. In FIG. 1C, the valve member 110 starts to degrade. This degradation may take place in parallel to the time at which a fibrous capsule is formed around the glaucoma valve 100. This may take place during the time of about 8 to about 12 weeks from implantation.

FIG. 2A to FIG. 2D are schematic diagrams of a glaucoma valve 200 according to various embodiments of the second aspect of the present invention. FIG. 2C shows a glaucoma valve 200 according to an embodiment of the second aspect of the present invention. The valve has a first flow channel 205 and a second flow channel 215. The second flow channel 215 is arranged in parallel to the first flow channel 205. The second flow channel 215 may be completely sealed with a degradable polymer 210, such that in use, the polymer 210 degrades to allow a fluid to flow through the first flow channel 205. FIG. 2D shows a glaucoma valve 200 according to another embodiment. The valve has a first flow channel 205 and a second flow channel 215. In this embodiment, the first flow channel 205 is connected in parallel to the second flow channel 215. Fluid may be allowed to flow through an inlet 220 which then flows to both the first flow channel 205 and the second flow channel 215. As the first flow channel 205 is completely sealed with a degradable polymer 210, therefore, the fluid may flow out via the second flow channel 215 only. The degradable polymer 210 in the first flow channel 205 may be degraded to a sufficient extent with time such that the fluid flows out from the first flow channel 205.

FIG. 3A and FIG. 3B are schematic diagrams depicting equivalent circuits in a prior art GDD. In FIG. 3A, IOP(A) may be determined by the equation: IOP(A)=ambient pressure+ΔP_GDD. In FIG. 3B, due to formation of the fibrous capsule, there is an additional flow resistance and pressure drop due to the capsule. R_Capsule refers to the flow resistance of the fibrous capsule. ΔP_Capsule denotes the pressure drop across the fibrous capsule. IOP after fibrous capsule formation is denoted by IOP(B) and may be determined by the equation: IOP(B)=ambient pressure+ΔP_GDD+ΔP_Capsule. Therefore, IOP (B) may be greater than IOP(A) by an amount ΔP_Capsule, which may be attributed to the fibrous capsule formed in the prior art GDD.

FIG. 5A and FIG. 5B are schematic diagrams depicting equivalent circuits in a GDD according to embodiments of the second aspect of the present invention. In FIG. 5A, as the first flow channel is completely sealed with a degradable polymer, fluid flows through the second flow channel only. ΔP_GDD denotes the pressure drop across the GDD. IOP(A) denotes the intraocular pressure and may be determined by the equation: IOP(A)=ambient pressure+ ΔP_GDD. In FIG. 5B, the polymer in the first flow channel has degraded, and fluid can flow through both the first flow channel and the second flow channel. The resultant pressure drop across the valve is denoted by ΔP_mGDD, which is of a lower value compared to ΔP_GDD. IOP after fibrous capsule formation is denoted by IOP(B) and may be determined by the equation: IOP(B)=ambient pressure+ ΔP_mGDD+ΔP_Capsule. The lower ΔP_mGDD may be sufficient to offset the increase in pressure drop due to ΔP_Capsule. As such, IOP(B) may remain the same or may even be lower than IOP(A).

DETAILED DESCRIPTION

In a first aspect, the invention relates to a glaucoma valve. The glaucoma valve includes a flow channel having an inlet and an outlet. A valve member is connected to the outlet of the flow channel, in which the valve member comprises a degradable polymer. In some embodiments, the valve member can be formed from a mixture or combination of a degradable polymer and a non-degradable polymer.

By using a degradable polymer such as a biodegradable elastomer to form the valve member or at least part of the valve member, upon implantation of the glaucoma valve in the eye, the valve member may degrade gradually due to action of the aqueous fluid in the body with the biodegradable elastomer. At the same time, a fibrous capsule may be formed around the glaucoma valve as part of the natural healing process. In a conventional GDD, formation of the fibrous capsule increases the flow resistance of the glaucoma valve by at least partially obstructing the drainage of aqueous humor fluid from the eye, thereby resulting in a higher IOP value compared to the period of time before capsule formation. However, using a glaucoma valve according to various embodiments of the present invention, the flow resistance of the glaucoma valve may be maintained at a constant level or decreases with time as the polymer degrades. As such, the IOP may be maintained at a constant level.

The term "valve" refers to a device for regulating and/or directing the flow of a fluid. Examples of a valve include, but are not limited to, a check valve, a globe valve, a gate valve, a ball valve, a needle valve, a solenoid valve and a spool valve. Accordingly, the term "glaucoma valve" as used herein refers to a valve used in glaucoma drainage devices.

The glaucoma valve includes a flow channel having an inlet and an outlet. The flow channel acts as a conduit for fluid to flow through, and may be of any suitable length. For example, the flow channel may have a length of about 5 mm to about 25 mm, such as about 5 mm, 10 mm, 15 mm, 20 mm, or 25 mm.

The cross-section of the flow channel may be of any shape, such as a square, a triangle, a rectangle, an oval or a circle. Generally, the flow channel is in the form of a cylindrical tube. The cross-section of the flow channel may be characterized by its diameter. The term "diameter" as used herein refers to the maximal length of a straight line segment passing through the center of a figure and terminating at the periphery. Accordingly, the outer diameter of the flow channel refers to the maximal length of a line segment passing through the centre and connecting two points on the outer wall of the flow channel, whereas the inner diameter of the flow channel refers to the maximal length of a line segment passing through the centre and connecting two points on the inner wall of the flow channel. Although the term "diameter" is used normally to refer to the maximal length of a line segment passing through the centre and connecting two points on the periphery of a circle, it is also used herein to refer to the maximal length of a line segment passing through the centre and connecting two points on the periphery of other shapes, such as a square, triangle, rectangle, oval or circle.

The diameter of the flow channel may be of any suitable length. For example, the outer diameter of the flow channel may be from about 0.1 mm to about 1 mm, such as about 0.1 mm, 0.2 mm, 0.4 mm, 0.6 mm, 0.8 mm or 1 mm. The inner diameter of the respective flow channel is smaller than its outer diameter, and is dependent on the wall thickness of the flow channel. For example, the inner diameter of the flow channel may be from about 0.05 mm to about 0.5 mm, such as about 0.05 mm, 0.1 mm, 0.2 mm, 0.3 mm, 0.4 mm or 0.5 mm.

The flow channel may be formed from any material that is suitable for implanting into a living body such as a human. For example, the flow channel may be formed from a medical grade polymer such as, but are not limited to, medical grade elastomers, medical grade polyurethane, high density polyethylene, polyethylene, polypropylene and nylon.

A valve member may be connected to the outlet of the flow channel. The term "valve member" as used herein refers to a component in a valve that is used as an obstruction to control or restrict fluid flow through the valve. The valve member may extend outwards from the flow channel, and may be of any suitable length. For example, the valve member may have a length of about 1 mm to about 10 mm, such as about 1 mm, 2 mm, 4 mm, 6 mm, 8 mm, or about 10 mm. The valve member may be of any suitable shape. For example, the valve member may be a cylindrical tube, a cube, a sphere or may be irregularly shaped.

The valve member may have an opening which is normally closed. In some embodiments, the opening is present as an elongated slit-like opening on the valve member. The opening on the valve member may be triggered to open when the IOP exceeds a predetermined pressure level of the valve member. As such, IOP may be maintained at a level close to the predetermined pressure level of the valve member. For example, the valve member may have a predetermined pressure level of about 10 mm Hg to about 14 mm Hg, such as about 10 mm Hg, 11 mm Hg, 12 mm Hg, 13 mm Hg or 14 mm Hg. In one embodiment, the valve member has a predetermined pressure level of about 10 mm Hg. When the IOP exceeds 10 mm Hg, the valve member opens to allow excess aqueous humor fluid to flow out from the eye, via the tube and out through the opening on the valve member. In this way, IOP may be maintained at a pressure level of about 10 mm Hg. The predetermined pressure level of the valve member may depend, for example, on the dimension of the valve member, the size and/or shape of the opening on the valve member, the types of polymer and the tensile modulus of the polymers that is used to form the valve member.

The valve member may be formed from a degradable polymer. As used herein, the term "degradable" refers to a material having a structure which can decompose to smaller molecules under certain conditions, such as temperature, abrasion, pH, ionic strength, electrical voltage, current effects, radiation and biological means.

The valve member may comprise a biodegradable polymer. In some embodiments, the valve member consists of a biodegradable polymer. The term "biodegradable" refers to a substance which can be broken down biologically, for example, when exposed to conditions found in the human body or under environmental conditions commonly found in nature. Examples of a biodegradable polymer include, but are not limited to, polymers and oligomers of glycolide, lactide, polylactic acid, polyesters of a-hydroxy acids, including lactic acid and glycolic acid, such as the poly(a-hydroxy) acids including polyglycolic acid, poly-DL-lactic, poly-L-lactic acid, and terpolymers of DL-lactide and glycolide; e-caprolactone and e-caprolactone copolymerized with polyesters; polylactones and polycaprolactones including poly(e-caprolactone), poly(8-valerolactone) and poly (gamma-butyrolactone); polyanhydrides; polyorthoesters; other hydroxy acids; polydioxanone; and other biologically degradable polymers that are non-toxic or are present as metabolites in the body.

The biodegradable polymer may be a biodegradable elastomer. The term "elastomer" refers to polymers having the ability to undergo deformation under the influence of a force and regain its original shape once the force is removed. The biodegradable elastomer according to various embodiments of the present invention may be polylactic acid (PLA), polycaprolactone (PCL), poly(glycolide) (PLGA), a copolymer of PLA and PCL, a copolymer of PLA, PCL and PLGA, a copolymer of PLA, PCL and trimethylene carbonate (TMC), a copolymer of PLA, PCL, TMC and polyurethane (PU).

In various embodiments, the biodegradable elastomer is a copolymer of PLA and PCL. The copolymer of PLA and PCL may have a molar ratio of about 7:3. In some embodiments, a multiblock copolymer of PLA and PCL or a triblock copolymer of PLA and PCL having PLA as the end-blocks and PCL as the middle block may be used as the biodegradable elastomer. The multiblock copolymer PLA and PCL may be PCL-PLA-co-PLA-PCL, having a caprolactone content of about 30% in the first block and a lactic acid content of about 30% in the second block. The PLA end-blocks of the triblock copolymer of PLA and PCL may have a crystallinity of about 10% to about 20%.

In various embodiments, the biodegradable elastomer is a copolymer of PLA, PCL and PLGA. The copolymer of PLA, PCL and PLGA may be a triblock copolymer having PLA as the end-blocks and a random copolymer of PCL and PLGA as the middle block.

In some embodiments, the biodegradable elastomer is a copolymer of PLA, PCL and TMC. The copolymer of PLA, PCL and TMC may be a triblock copolymer having PLA as the end-blocks and a random copolymer of PCL and TMC as the middle block. The PLA end-blocks of the triblock copolymer may have a crystallinity of about 10% to about 20%.

In further embodiments, the biodegradable elastomer is a copolymer of PLA, PCL, TMC and PU. The copolymer of PLA, PCL, TMC and PU may be a polyurethane with PCL/PLA and PCL/TMC soft segments.

The valve member may degrade at the opening, thereby resulting in a larger opening and allowing a larger volume of aqueous humor to be drained out from the eye with time. The time at which the valve member starts to degrade and/or the time required for the valve member to degrade may be designed to coincide with the time a fibrous capsule starts to develop around the valve and/or the time required for the fibrous capsule to develop around the valve. In this way, a steady rate aqueous outflow may result and may lead to a lesser extent of IOP fluctuation. Degradation of the valve member can take place over a time period ranging from a few seconds to a few days or months. The time period required for the valve member to degrade can be dependent on a few parameters, for example, constituent of valve member such as types of polymer used and the level of crystallinity of the polymer(s), temperature, pH, and amount of aqueous fluid present. Under physiological conditions, that means in an animal body, degradation is in general about 2 months. In some embodiments, the degradation time of the valve member is about 3 weeks to about 12 weeks. In some embodiments, the valve member is completely degraded, leaving only the flow channel.

The polymer used to form the valve member may exhibit different tensile properties, which may affect the predetermined pressure level of the valve member. Generally, the polymer that is used to form the valve member may have a Young's modulus of about 1 MPa to about 30 MPa, such as about 1, 2, 4, 10, 20, or 30 MPa. In one embodiment, the polymer that is used to form the valve member has a Young's modulus of about 10 MPa. As used herein, the term "Young's modulus" refers to a mechanical property of a material, expressed as a ratio of stress to corresponding strain when the material behaves elastically under tension. The Young's modulus of the polymer used to form the valve member can be measured using any suitable method. For example, the Young's modulus of the polymer can be measured using the standard test method for tensile properties of plastics described in American Society for Testing and Materials (ASTM) Standard D882-09.

The polymer used to form the valve member may have an elongation to break percentage of greater than about 100%. As used herein, the term "elongation to break" refers to the percent elongation of a material under an applied tensile loading at the moment of rupture (break point). Generally, the percent elongation to break is determined based on original length of the polymer under test. The elongation to break percentage of the polymer used to form the valve member can be measured using any suitable method, such as that mentioned herein for determining the Young's modulus of the polymer.

In various embodiments, the elastic recovery value of the polymer used to form the valve member is greater than about 80%. The term "elastic recovery value" as used herein refers to the percentage of the elastic deformation to the total deformation of the polymer. The elastic recovery value of the polymer used to form the valve member can be determined using any suitable method. For example, in one test for determining the elastic recovery value of the polymers, the polymers under test may be prepared in the same way as that mentioned herein for determining the Young's modulus of the polymers. Subsequently, polymer samples may be pulled to about 100%, 200% and 300% elongations at about 10 mm/min using a microtester. After the specific elongations are achieved, the microtester may be stopped and the sample may be taken out of the microtester. Depending on the tensile properties of the polymers, the polymer samples may recover at different extents to its original dimensions. The final sizes, such as length and breath, of the sample may be measured after the samples are allowed to recover for 5 minutes. The elastic recovery value may be calculated based on the percentage change in size of the polymer samples from its elongated state to its recovered state.

Figure 1A:
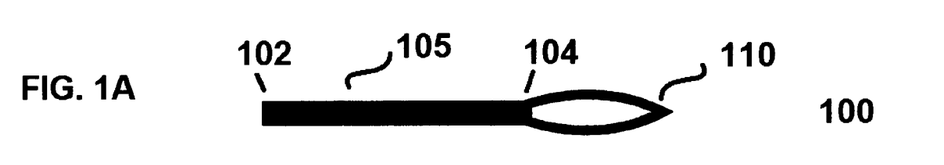
FIG. 1A shows a glaucoma valve 100 formed from a flow channel 105 and a valve member 110. The flow channel 105 has an inlet 102 and an outlet 104. The valve member 110 is connected to the outlet 104 of the flow channel 105.
Figure 1B:
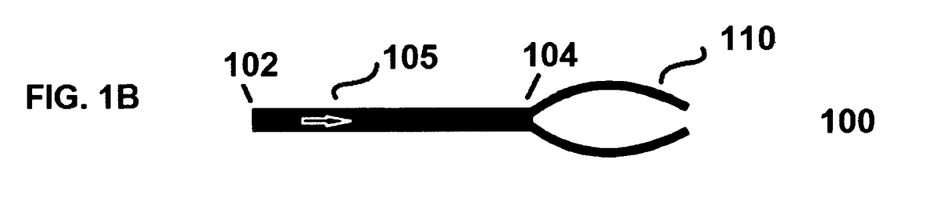
FIG. 1B depicts the behavior of the glaucoma valve 100 when a fluid flows through it. The fluid flows into the flow channel 105 via the inlet 102 and out via the outlet 104. When the intraocular pressure (IOP) is greater than the opening pressure of the valve, the valve member 110 opens to allow outflow of the fluid. This may take place from the time at which the GDD is first implanted into the eye to about 8 weeks from implantation.
Figure 1C:
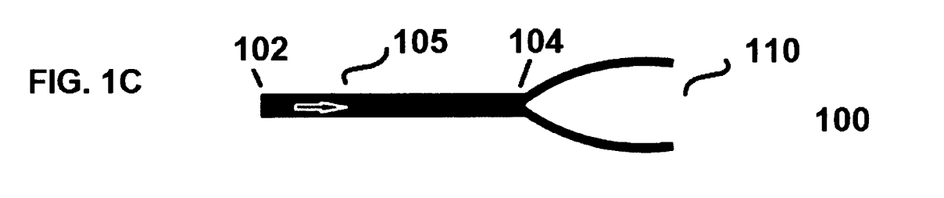
Figure 1D:
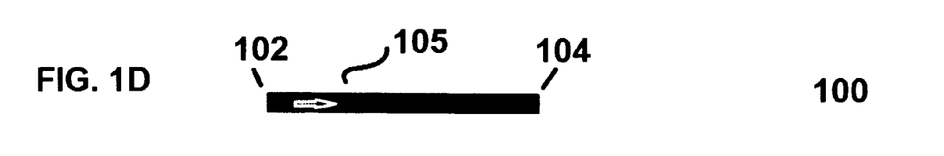
FIG. 1D shows that the valve member 110 has completely degraded, leaving behind the flow channel 105 only. This may take place after about 12 weeks from implantation.

FIG. 1A to FIG. 1D are schematic diagrams of a glaucoma valve 100 according to an embodiment of the present invention. FIG. 1A shows a glaucoma valve 100 formed from a flow channel 105 and a valve member 110. The flow channel 105 has an inlet 102 and an outlet 104. The valve member 110 is connected to the outlet 104 of the flow channel 105. FIG. 1B depicts the behavior of the glaucoma valve 100 when a fluid flows through it. The fluid flows into the flow channel 105 via the inlet 102 and out via the outlet 104. When the intraocular pressure (IOP) is greater than the opening pressure of the valve, the valve member 110 opens to allow outflow of the fluid. This may take place from the time at which the GDD is first implanted into the eye to about 8 weeks from implantation. In FIG. 1C, the valve member 110 starts to degrade. This degradation may take place in parallel to the time at which a fibrous capsule is formed around the glaucoma valve 100. This may take place during the time of about 8 to about 12 weeks from implantation. FIG. 1D shows that the valve member 110 has completely degraded, leaving behind the flow channel 105 only. This may take place after about 12 weeks from implantation.

The valve member may further include a steroid. Steroids are widely used as therapeutic agents for various inflammatory diseases. For the treatment of glaucoma using implantation of a GDD, steroids may be used to reduce post-operative inflammation. Examples of steroid that may be used in the present invention include, but are not limited to, dexamethasone, fluocinolone, fluocinolone acetonide, triamcinolone, triamcinolone acetonide, salts thereof, derivatives thereof, and mixtures thereof. The steroid may be mixed with the polymer used to form the valve member or may be present as a coating on the valve member. As such, there may be controlled release of the steroid constituent or coating at a specific surgical site in a sustained manner, which may make the drug action more effective compared to the administration of eye drops comprising the steroid. Furthermore, as the steroids are released in therapeutic levels concurrently with the degradation of the polymer of the glaucoma valve, this may alleviate the need for self-administration of the eye drops by the patients thereby preventing issues with patient compliance with the medication protocol and potential toxicity from incorrect dosages.

According to a second aspect, the invention relates to a glaucoma valve. The valve comprises a first flow channel. The interior of the first flow channel is at least in part coated with a degradable polymer, such that in use, the polymer degrades to allow a greater flow of fluid through the flow channel. The degradable polymer may be a biodegradable polymer. Generally, any biodegradable polymer can be used in the present invention. Examples of biodegradable polymers that can be used have already been described herein. In some embodiments, the biodegradable polymer is a biodegradable elastomer.

Figure 2A:
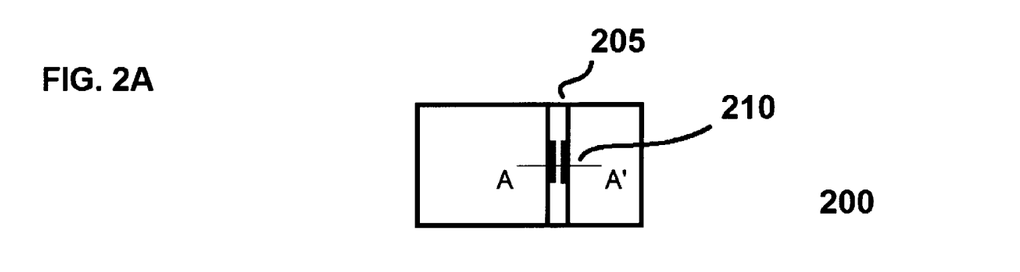
FIG. 2A shows a glaucoma valve 200 according to an embodiment, the valve having a first flow channel 205. The interior of the first flow channel 205 is at least in part coated with a degradable polymer 210, such as a biodegradable polymer, for example.
Figure 2B:
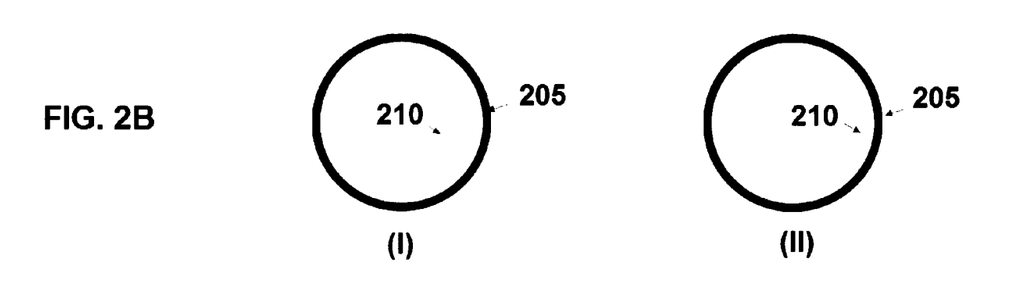
FIG. 2B(I) shows a sectional view of the flow channel 205 along the line A-A' in the embodiment shown in FIG. 2A. In use, the polymer 210 may degrade to result in the flow channel 205 having a larger diameter allowable for fluid flow, such as that shown in FIG. 2B(II).

FIG. 2A shows a glaucoma valve 200 according to an embodiment, the valve having a first flow channel 205. The interior of the first flow channel 205 is at least in part coated with a degradable polymer 210. FIG. 2B(I) shows a sectional view of the flow channel 205 along the line A-A' in the embodiment shown in FIG. 2A. In use, the polymer 210 may degrade to result in the flow channel 205 having a larger diameter allowable for fluid flow, such as that shown in FIG. 2B(II). In the early stages of GDD operation, the inner diameter of the flow channel may be small due to the coated polymer, thereby providing a higher flow resistance. With time, a fibrous capsule may be formed around the GDD. While the fibrous capsule forms, the coated polymer may dissolve or degrade, thereby providing a larger diameter for fluid flow and which may result in a lower flow resistance. Since the coated polymer may act as an obstruction to control or restrict fluid flow through the valve, it functions like a valve member such as that defined herein.

Figure 2C:
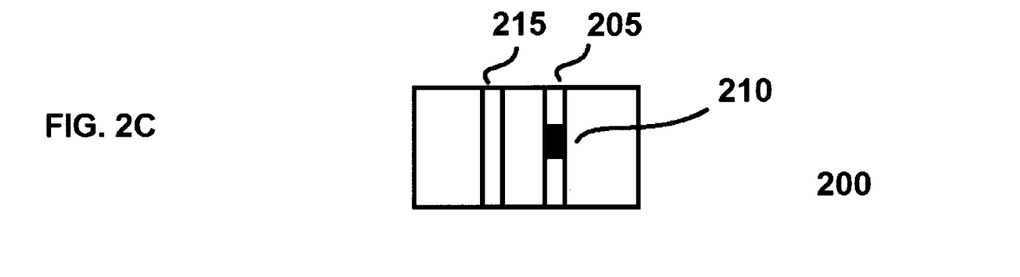

In some embodiments, the glaucoma valve further comprises a second flow channel, such as that illustrated in FIG. 2C for example. FIG. 2C shows a glaucoma valve 200 according to an embodiment of the second aspect of the present invention. The valve has a first flow channel 205 and a second flow channel 215. The second flow channel 215 is arranged in parallel to the first flow channel 205. The second flow channel 215 may be completely sealed with a degradable polymer 210 such that no fluid is allowed to pass through the first channel when the glaucoma valve is first used. Upon degradation of the polymer, the first flow channel may allow a fluid to flow through it. In this way, the polymer in the first channel may act like a valve member to control and/or restrict fluid flow through the valve. The second flow channel, on the other hand, may always allow a fluid to flow through.

Figure 2D:
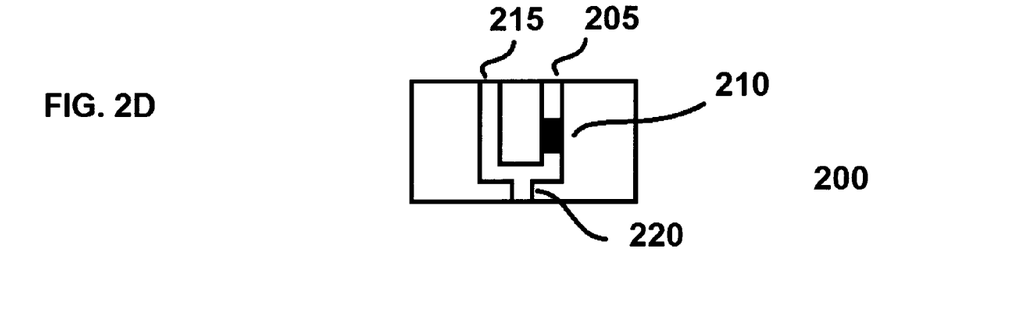
Figure 3A:
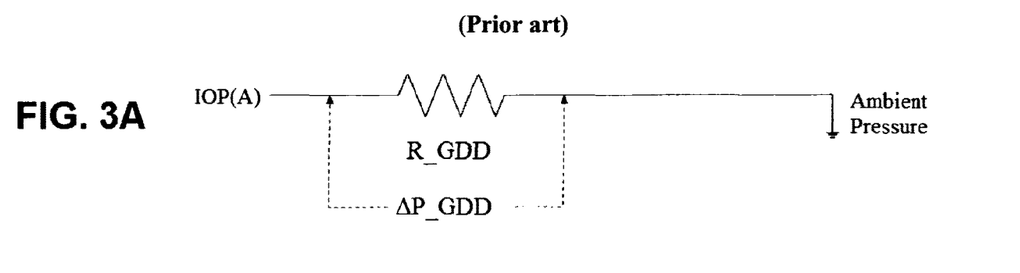
FIG. 3A depicts an equivalent circuit in a prior art GDD before fibrous capsule formation.
Figure 3B:
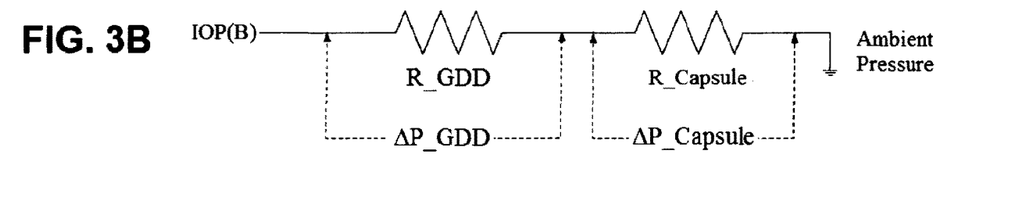
FIG. 3B depicts the equivalent circuit for the same prior art GDD after fibrous capsule formation. In the figures, IOP(A) denotes the intraocular pressure, R_GDD denotes the flow resistance of the prior art GDD, and ΔP_GDD denotes the pressure drop across the prior art GDD.
Figure 4:
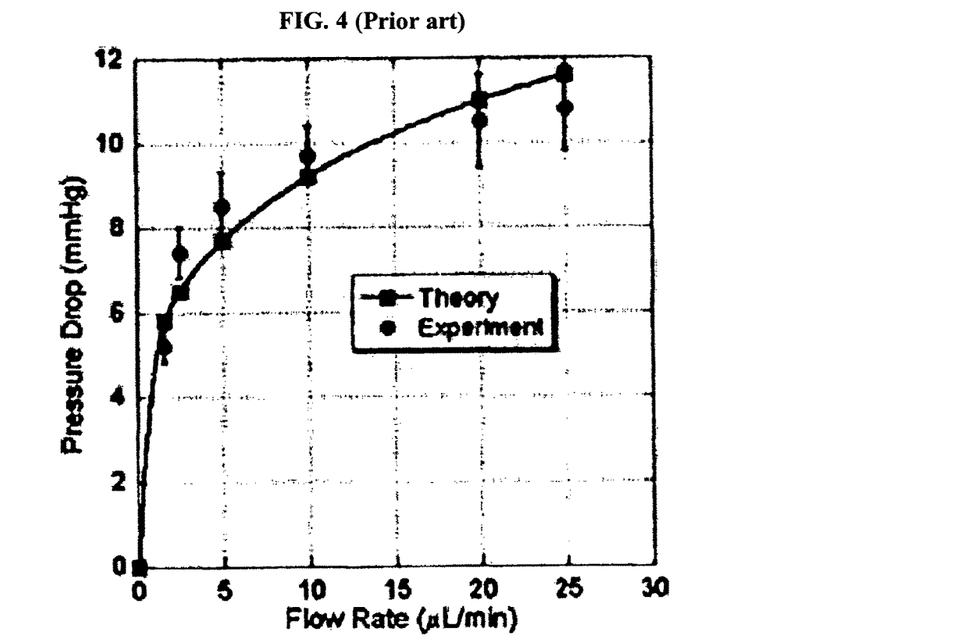
FIG. 4 is a graph showing pressure drop across a commercially available Ahmed Glaucoma Valve (AGV).
Figure 5A:
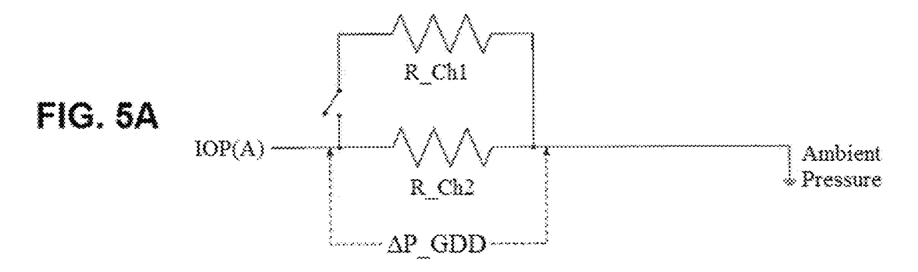
FIG. 5A depicts an equivalent circuit in a GDD in which the first flow channel is completely sealed with a degradable polymer and before fibrous capsule formation.
Figure 5B:
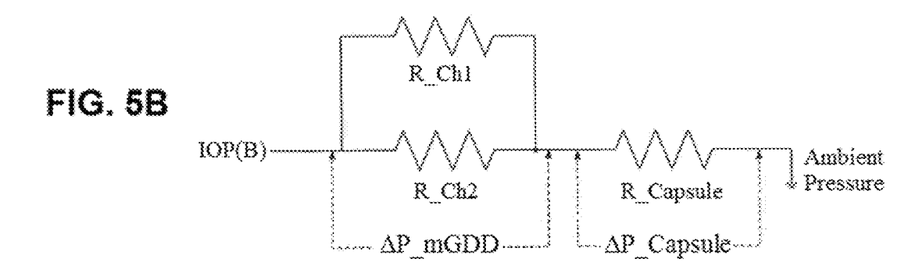
FIG. 5B depicts the equivalent circuit for the same GDD in which the degradable polymer in the first flow channel has degraded and in which a fibrous capsule has formed around the second channel of the GDD. In the figures, R_Ch1 denotes the flow resistance of the first flow channel, R_Ch2 denotes the flow resistance of the second flow channel, and R_Capsule denotes the flow resistance of the fibrous capsule. The first flow channel is arranged in parallel to the second flow channel.

FIG. 2D shows a glaucoma valve 200 according to another embodiment, the valve having a first flow channel 205 and a second flow channel 215. In this embodiment, the first flow channel 205 is connected in parallel to the second flow channel 215. Fluid may be allowed to flow through an inlet 220 which then flows to both the first flow channel 205 and the second flow channel 215. As the first flow channel 205 is completely sealed with a degradable polymer 210, therefore, the fluid may flow out via the second flow channel 215 only. The degradable polymer 210 in the first flow channel 205 may be degraded to a sufficient extent with time such that the fluid flows out from the first flow channel 205.

The time at which the polymer in the first channel flow starts to degrade and/or the time required for the polymer in the first channel to degrade may be designed to match the time at which a fibrous capsule starts to form around the valve and/or the time required for a fibrous capsule to form around the valve. As part of the natural wound healing process after invasive surgery, a fibrous capsule may gradually form about the glaucoma valve. The extra flow resistance conferred by the fibrous capsule may result in a higher than the initial level of IOP before capsule formation. In embodiments of the present invention, as the second flow channel is connected in parallel to the first flow channel, the resultant flow resistance of the glaucoma valve after capsule formation may be maintained or may even be lower than the initial flow resistance prior to capsule formation.

Flow resistance of the second flow channel may be designed to provide an acceptable IOP before fibrous capsule formation. For example, an acceptable IOP may be about 10 mm Hg to about 14 mm Hg. The flow resistance of the second flow channel may depend on the dimensions of the flow channel such as the length and diameter, and the type of material that is used to form the channel.

According to a third aspect, the invention relates to a casing for containing a glaucoma valve. The casing may have a top portion and a bottom portion. Either or both the top portion and the bottom portion may comprise a degradable polymer, such as a biodegradable polymer. In some embodiments, either or both the top portion and the bottom portion may be formed from a mixture of a degradable polymer and a non-degradable polymer. In various embodiments, the degradable polymer is a biodegradable polymer, such as a biodegradable elastomer. In some embodiments, the biodegradable polymer is PLGA. The PLGA may have a lactic acid to glycolic acid ratio of about 3:1 to about 9:1. The biodegradable polymer may have a Young's modulus of about 10 to about 1000 MPa. The biodegradable polymer may have a degradation time of about 3 weeks to about 12 weeks. In some embodiments, both the top portion and the bottom portion of the casing consist of a biodegradable polymer. The use of biodegradable polymer to form the casing may lead to reduction in hypertony, which may take place in a 3 weeks to a 6 weeks timeframe.

Figure 9:
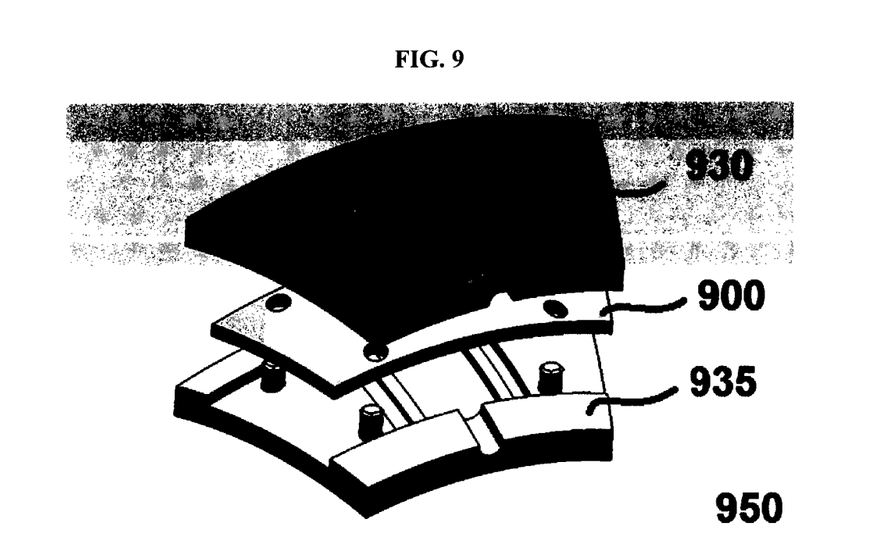
FIG. 9 is a schematic diagram of a GDD 950 according to the fourth aspect of the present invention. The GDD 950 includes a casing comprised of a top cover 930 and a bottom cover 935, and a glaucoma valve 900. The glaucoma valve 900 may be encased in the casing.

FIG. 9 is a schematic diagram of a GDD 950 according to the fourth aspect of the present invention. The GDD 950 includes a casing comprised of a top cover 930 and a bottom cover 935, and a glaucoma valve 900. The glaucoma valve 900 may be encased in the casing. The casing maybe integrally formed with the glaucoma valve. In some embodiments, the casing and the glaucoma valve may be formed separately and subsequently assembled together.

In a fourth aspect, the invention relates to a glaucoma drainage device comprising a glaucoma valve according to the first or the second aspect, and/or a casing according to the third aspect.

Figures 6A, 6B, 6C, 6D, 6E:
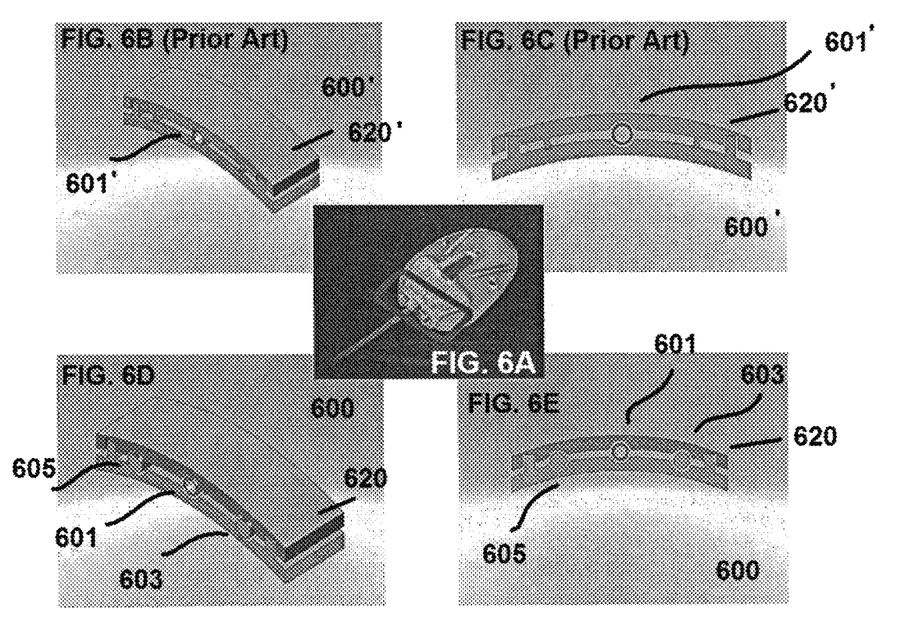
FIG. 6A is a schematic diagram showing a possible location of a GDD valve in a GDD.
FIG. 6B is a schematic diagram showing a prior art GDD valve 600', including a flow channel 601' that is contained in a casing 620'.
FIG. 6C is a schematic diagram showing a side view of the prior art GDD valve 600'.
FIG. 6D is a schematic diagram showing a GDD valve 600 according to an embodiment of the second aspect of the present invention, including a first flow channel 601, a second flow channel 603 and a third flow channel 605. The flow channels are contained in a casing 620, which may be formed from a biodegradable polymer according to an embodiment of the third aspect of the invention. The second flow channel 603 and a third flow channel 605 may be completely sealed with a degradable polymer.
FIG. 6E is a schematic diagram showing a side view of the GDD valve 600 according to an embodiment of the second aspect of the present invention.

FIG. 6A is a schematic diagram showing a possible location of a GDD valve in a GDD. FIG. 6B is a schematic diagram showing a prior art GDD valve 600', including a flow channel 601' that is contained in a casing 620'. FIG. 6C is a schematic diagram showing a side view of the prior art GDD valve 600'. FIG. 6D is a schematic diagram showing a GDD valve 600 according to an embodiment of the second aspect of the present invention, including a first flow channel 601, a second flow channel 603 and a third flow channel 605. The flow channels are contained in a casing 620, which may be formed from a biodegradable polymer. The second flow channel 603 and a third flow channel 605 may be at least partially sealed with a degradable polymer. FIG. 6E is a schematic diagram showing a side view of the GDD valve 600 according to an embodiment of the second aspect of the present invention.

In a fifth aspect, the invention relates to use of a glaucoma drainage device according to the fourth aspect for the drainage of aqueous humor in an eye.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1: Polymer

Poly(ε-caprolactone) (PCL) and polylactide (PLA) are examples of biodegradable polymers with different degradation and mechanical behavior. A group of complex copolymers (PCL-PLA)-b-(PLA-PCL) have been synthesized in the lab, with about 30% of PCL in the first block and about 30% of PLA in the second block (denoted herein as "First Group"). The targeted weight average molecular weight is 20 K for each of the two blocks. The copolymers formed have a Young's modulus of about 10 MPa.

A second group of PCL and PLA copolymers were formed with a different molecular weight to test its suitability to be used as the glaucoma valve (denoted herein as "Second Group"). The polymer is (PCL-PLA)-b(PLA-PCL), containing about 30% of PCL in the first block and about 30% of PLA in the second block. The targeted weight average molecular weight is 40 K for each of the two blocks. The polymer was dissolved in tetrahydrofuran (THF) and film casted. The film thickness is about 170 µm.

Example 2: Soak Test

Figure 7:
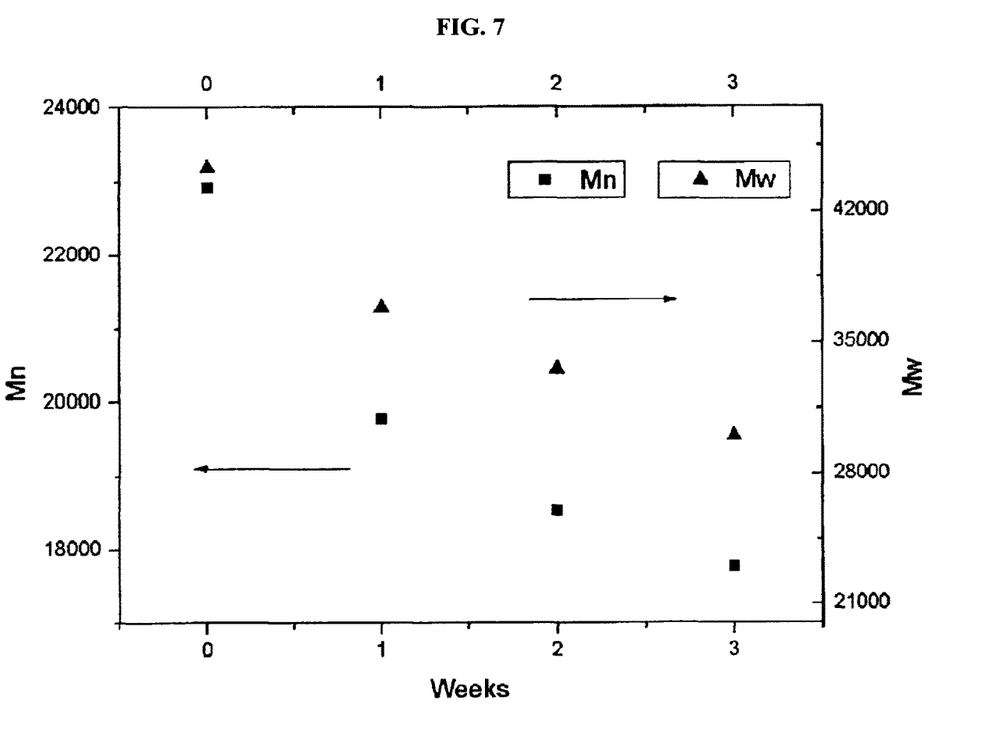
FIG. 7 is a graph showing the loss of molecular weight of a PCL-PLA copolymer.

The copolymers were soaked in phosphate buffered saline (PBS) at 37° C. FIG. 7 is a graph showing the loss of molecular weight of the "Second Group" PCL-PLA copolymer. Referring to the graph, Mn denotes the number average molecular weight of the copolymers, and Mw denotes the weight average molecular weight of the copolymers. As can be seen from the figure, there was a 22% drop in Mn and 32% drop in Mw in the first three weeks of soaking.

Figure 8:
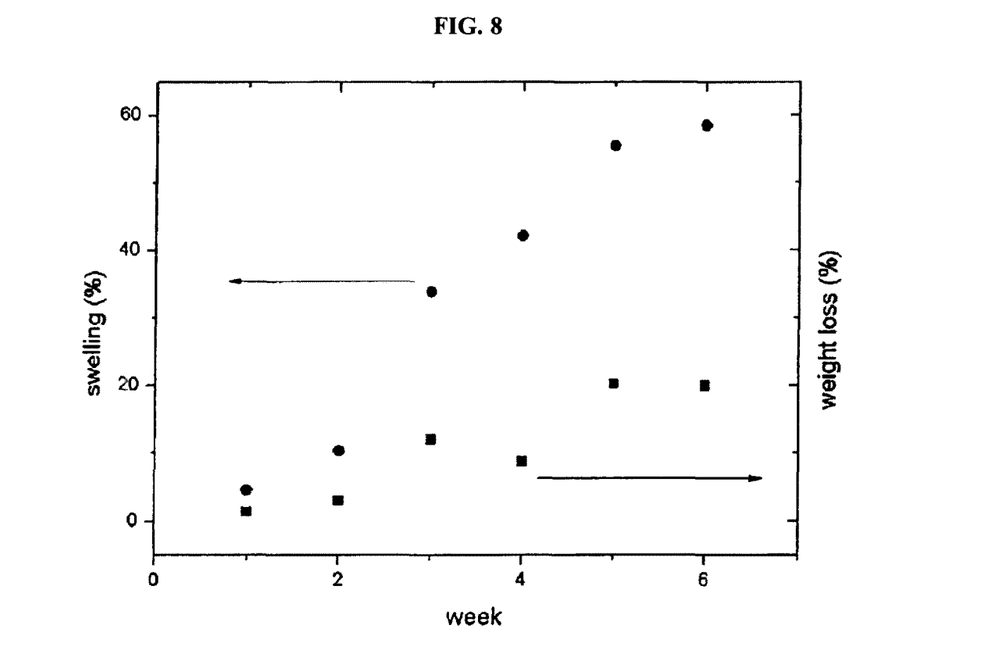
FIG. 8 is a graph showing the swelling and weight loss of a PCL-PLA copolymer soaked in phosphate buffered saline (PBS) at 37° C.

FIG. 8 is a graph showing the swelling and weight loss of the "Second Group" PCL-PLA copolymer. As can be seen from the graph, there was about 20% weight loss observed in the first six weeks.

As can be seen from the results obtained, the rate of reduction of the molecular weight of the PCL-PLA copolymer suggests that it is suitable for use as a biodegradable polymer in various aspects of the present invention.

Example 3: Pressure-Flow Measurement

Figure 10:
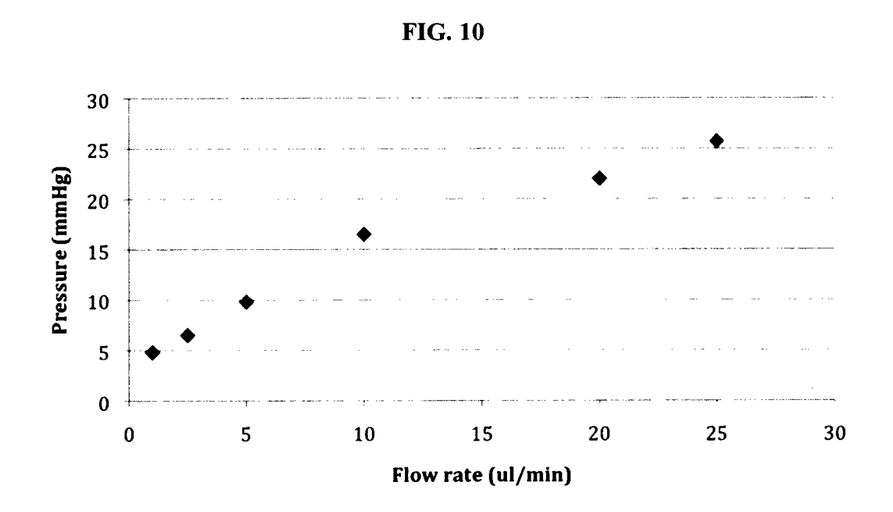
FIG. 10 is a graph showing pressure drop of a GDD according to an embodiment of the invention against flow rate.

A PCL-PLA copolymer is used to form a valve member with a thickness of about 100 µm of a glaucoma valve according to the first aspect of the invention. The pressure drop at a given flow rate of a GDD comprising the glaucoma valve is measured using de-ionized water and results are plotted in FIG. 10. FIG. 10 is a graph showing pressure drop of the GDD against flow rate. As shown from the figures, the pressure drop increases non-linearly with an increase in flow rate and the pressure drop at 2.5 ul/min is about 8 mmHg.

Example 4: Pressure-Flow Measurement with the Effect of Degradation

Figure 11:
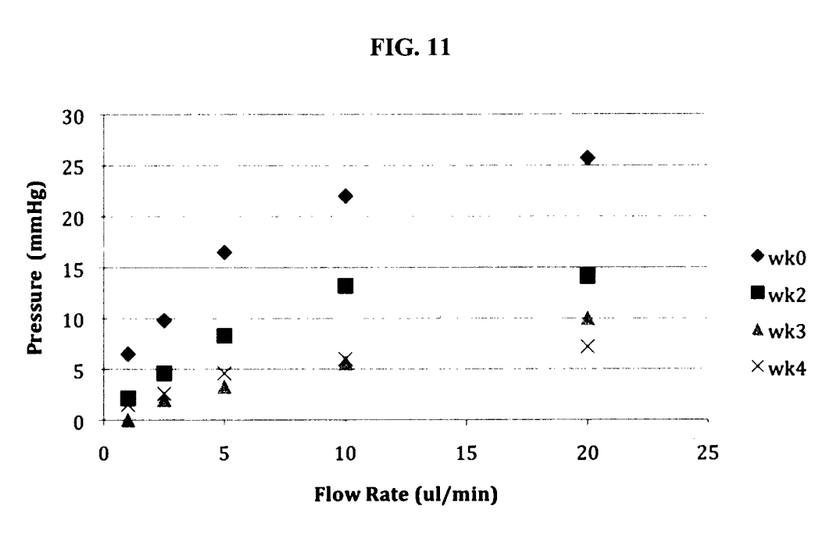
FIG. 11 is a graph showing pressure drop of a GDD according to an embodiment of the invention as a function of time ranging from week 0 (denoted as wk 0) to week 4 (denoted as wk 4) at different flow rates.

The same PCL-PLA copolymer as that used in Example 3 is used to form a valve member with a thickness of about 100 µm of a glaucoma valve according to the first aspect of the invention. A GDD comprising the glaucoma valve is soaked in PBS at 37° C. The pressure-flow behavior of the GDD is measured weekly, and results are plotted in FIG. 11. FIG. 11 is a graph comparing the pressure drop behavior of the GDD as a function of time ranging from week 0 (denoted as wk 0) to week 4 (denoted as wk 4) at different flow rates. As can be seen from the graph, the pressure drop at 2.5 ul/min decreased from about 10 mmHg to about 3 mmHg in a time duration of four weeks.

The invention claimed is:

1. A glaucoma valve, the valve comprising
   a) a flow channel having an inlet and an outlet; and
   b) a valve member connected to the outlet of the flow channel, wherein the valve member comprises a degradable polymer and a steroid, wherein the valve member is adapted to start degradation when a fibrous capsule is developing around the valve, wherein the steroid is mixed with the degradable polymer to form the valve member, and wherein the degradable polymer is configured to degrade during formation of the fibrous capsule so as to release the steroid in therapeutic levels concurrently with degradation of the degradable polymer.

2. The glaucoma valve according to claim 1, wherein the polymer is a biodegradable elastomer.

3. The glaucoma valve according to claim 2, wherein the biodegradable elastomer is selected from the group consisting of polylactic acid (PLA), polycaprolactone (PCL), poly (glycolide) (PLGA), a copolymer of PLA and PCL, a copolymer of PLA, PCL and PLGA, a copolymer of PLA, PCL and trimethylene carbonate (TMC), a copolymer of PLA, PCL, TMC and polyurethane (PU).

4. The glaucoma valve according to claim 3, wherein the copolymer of PLA and PCL has a molar ratio of about 7:3.

5. The glaucoma valve according to claim 3, wherein the copolymer of PLA and PCL is selected from the group consisting of a multiblock copolymer of PLA and PCL, and a triblock copolymer of PLA and PCL having PLA as the end-blocks and PCL as the middle block.

6. The glaucoma valve according to claim 5, wherein the PLA end-blocks of the triblock copolymer of PLA and PCL has a crystallinity of about 10% to about 20%.

7. The glaucoma valve according to claim 3, wherein the copolymer of PLA, PCL and PLGA is a triblock copolymer having PLA as the end-blocks and a random copolymer of PCL and PLGA as the middle block.

8. The glaucoma valve according to claim 3, wherein the copolymer of PLA, PCL and TMC is a triblock copolymer having PLA as the end-blocks and a random copolymer of PCL and TMC as the middle block.

9. The glaucoma valve according to claim 8, wherein the PLA end-blocks of the triblock copolymer of PLA, PCL and TMC has a crystallinity of about 10% to about 20%.

10. The glaucoma valve according to claim 3, wherein the copolymer of PLA, PCL, TMC and PU is a polyurethane with PCL/PLA and PCL/TMC soft segments.

11. The glaucoma valve according to claim 6, wherein the polymer has a Young's modulus of about 1 MPa to about 30 MPa.

12. The glaucoma valve according to claim 6, wherein the polymer has an elongation to break percentage of greater than about 100%.

13. The glaucoma valve according to claim 6, wherein the polymer has an elastic recovery value of greater than about 80%.

14. The glaucoma valve according to claim 6, wherein the steroid is selected from the group consisting of dexamethasone, fluocinolone, fluocinolone acetonide, triamcinolone, triamcinolone acetonide, salts thereof, derivatives thereof, and mixtures thereof.

15. A glaucoma valve, the valve comprising a first flow channel, wherein the valve is adapted to start degradation when a fibrous capsule is developing around the valve, wherein the interior of the flow channel is at least in part coated with a degradable polymer comprising a steroid, wherein the steroid is mixed with the degradable polymer, such that in use, the polymer degrades during formation of the fibrous capsule to allow a greater flow of fluid and release of the steroid through the flow channel in therapeutic levels concurrently with degradation of the degradable polymer.

16. The glaucoma valve according to claim 15, wherein the polymer is a biodegradable polymer selected from the group consisting of polylactic acid (PLA), polycaprolactone (PCL), poly(glycolide) (PLGA), a copolymer of PLA and PCL, a copolymer of PLA, PCL and PLGA, a copolymer of PLA, PCL and trimethylene carbonate (TMC), and a copolymer of PLA, PCL, TMC and polyurethane (PU).

17. The glaucoma valve according to claim 15, further comprising a second flow channel, wherein the second flow channel is arranged in parallel or connected in parallel to the first flow channel.

18. The glaucoma valve according to claim 17, wherein the first flow channel is completely sealed with the polymer, such that in use, the polymer degrades to allow fluid to flow through the first flow channel.

19. A casing for containing a glaucoma valve, wherein the valve comprises
a) a flow channel having an inlet and an outlet; and
b) a valve member connected to the outlet of the flow channel, wherein the valve is adapted to start degradation when a fibrous capsule is developing around the valve, wherein the valve member comprises a degradable polymer and a steroid, wherein the steroid is mixed with the degradable polymer to form the valve member, and wherein the degradable polymer is configured to degrade during formation of the fibrous capsule so as to release the steroid in therapeutic levels concurrently with degradation of the degradable polymer;
the casing comprising
a) a top portion, and
b) a bottom portion,
wherein either or both the top portion and the bottom portion is formed from a biodegradable polymer.

* * * * *

UNITED STATES PATENT AND TRADEMARK OFFICE
CERTIFICATE OF CORRECTION

| | | |
|---|---|---|
| PATENT NO. | : 10,548,769 B2 | Page 1 of 1 |
| APPLICATION NO. | : 13/816631 | |
| DATED | : February 4, 2020 | |
| INVENTOR(S) | : Venkatraman et al. | |

It is certified that error appears in the above-identified patent and that said Letters Patent is hereby corrected as shown below:

In the Claims

Column 15,
Lines 4, 7, 10, and 13, "claim 6", each occurrence, should read --claim 1--.

Signed and Sealed this
Twenty-eighth Day of July, 2020

Andrei Iancu
*Director of the United States Patent and Trademark Office*